United States Patent
Sachs et al.

(10) Patent No.: US 9,002,079 B2
(45) Date of Patent: Apr. 7, 2015

(54) SYSTEMS AND METHODS FOR MOTION DETECTING FOR MEDICAL IMAGING

(75) Inventors: Jonathan Sachs, Haida (IL); Yaron Hefetz, Kibbutz alonim (IL)

(73) Assignee: General Electric Company, Schenectady, NY (US)

( * ) Notice: Subject to any disclaimer, the term of this patent is extended or adjusted under 35 U.S.C. 154(b) by 249 days.

(21) Appl. No.: 13/476,934

(22) Filed: May 21, 2012

(65) Prior Publication Data

US 2013/0310655 A1    Nov. 21, 2013

(51) Int. Cl.
| | | |
|---|---|---|
| A61B 5/113 | (2006.01) | |
| A61B 6/00 | (2006.01) | |
| A61B 5/055 | (2006.01) | |
| A61B 5/00 | (2006.01) | |
| A61B 5/0456 | (2006.01) | |

(52) U.S. Cl.
CPC ............. *A61B 5/055* (2013.01); *A61B 5/113* (2013.01); *A61B 6/541* (2013.01); *A61B 5/6892* (2013.01); *A61B 5/721* (2013.01); *A61B 5/0456* (2013.01); *A61B 2576/00* (2013.01)

(58) Field of Classification Search
None
See application file for complete search history.

(56) References Cited

U.S. PATENT DOCUMENTS

| | | | | |
|---|---|---|---|---|
| 6,798,199 | B2 * | 9/2004 | Larson et al. | 324/309 |
| 7,365,334 | B1 * | 4/2008 | Gordon | 250/363.04 |
| 2004/0116804 | A1 * | 6/2004 | Mostafavi | 600/428 |
| 2004/0249314 | A1 * | 12/2004 | Salla et al. | 600/595 |
| 2007/0053494 | A1 * | 3/2007 | Mostafavi | 378/98.12 |
| 2007/0280508 | A1 * | 12/2007 | Ernst et al. | 382/107 |
| 2011/0064295 | A1 * | 3/2011 | Gagnon et al. | 382/131 |
| 2012/0033868 | A1 * | 2/2012 | Ren et al. | 382/131 |
| 2012/0201428 | A1 * | 8/2012 | Joshi et al. | 382/107 |

* cited by examiner

*Primary Examiner* — Jon Chang
(74) *Attorney, Agent, or Firm* — Lucas Divine; General Electric Company

(57) ABSTRACT

Systems and methods for medical imaging are provided. One method includes obtaining image information including timing information and obtaining motion information corresponding to an external movement by a patient being imaged. Obtaining the motion information includes detecting motion of the patient with a sensing device that does not engage the patient. The motion information includes motion timing information. The method further includes associating the motion information with the image information using the image timing information and the motion timing information. The method further includes forming an image representative of a portion of the patient using the associated image and motion information.

13 Claims, 5 Drawing Sheets

SYSTEMS AND METHODS FOR MOTION DETECTING FOR MEDICAL IMAGING

BACKGROUND OF THE INVENTION

The subject matter disclosed herein relates generally to motion detecting, and more particularly to systems and methods for motion detecting for medical imaging.

Images of a subject, for example a portion of interest of a patient, may be obtained by a variety of different methods. Such methods include, as examples, single photon emission computed tomography (SPECT), positron emission tomography (PET), magnetic resonance imaging (MRI), and computed tomography (CT). These imaging systems typically form an image by performing one or more data acquisitions performed at discrete time intervals, with an image formed from a combination of the information obtained by the data acquisitions. For example, nuclear medicine (NM) imaging systems, use one or more image detectors to acquire imaging data, such as gamma ray or photon imaging data. The image detectors may be gamma cameras that acquire a view or views of emitted radionuclides (from an injected radioisotope) from a patient being imaged.

Performing a series of image acquisitions may take a considerable amount of time. For example, an image may be generated by data that is acquired over a time period of up to 15 minutes or more. Because the final image is reconstructed from a combination of portions of information obtained over time, any movement by a patient may result in blurring or other artifacts that reduce image quality or usability. However, it is frequently difficult for patients to remain still during the entire image acquisition process or portions thereof. For example, one form of motion frequently encountered in image acquisition is caused by breathing. For a certain imaging (or imaging portions) taking over 45 seconds, it may be difficult for patients to hold their breath that long. Similarly, patients may shift their weight or move in other fashions during image acquisition. Such movement of a patient relative to a detector or detectors results in inconsistencies between sets of data obtained over time relative to each other, and results in blurring or other artifacts. Certain presently known attempts to deal with patient movement are either uncomfortable, fail to provide a measure of magnitude for movement during image acquisition, fail to provide for differentiation and/or characterization of different types of movement or different positions taken by a patient, and/or fail to provide motion information in a timely and efficient manner.

For example, in NM an image may be reconstructed from acquired data. The reconstruction may involve creating a 3D image from a plurality of 2D images which were acquired by the camera. The image quality strongly depends on the duration of the data acquisition, to the point that to create a clinically useful image, about 15 minutes of data acquisition or more may be needed. For example, in certain known techniques, data is acquired with time stems or as a series of timely frames. Then, consecutive frames (of the same viewpoint) are compared. If motion is detected (by displacement of anatomical markers), the data is corrected by shifting the data in the frame. A final image is reconstructed from the (now corrected) totality of the frames. Or, a set of timely images may be reconstructed, each from frames taken at the same time. The consecutive images are compared. If motion is detected (by displacement of anatomical markers), the image is corrected by shifting the data in the image. A final image is created by summing all the (now corrected) totality of images.

However, such known techniques have a number of drawbacks. For example, the division of the data to time slots is arbitrary (as motion may occur at random times). Thus, it is likely that at least some of the frames includes data of "before & after" the motion. The blur caused by this frame cannot be corrected. Also, if the data is divided to many "time windows," the quality of the data in the frames (or in the image reconstructed from these frames) is poor. This can lead to a number of errors. For example, motion may not be detected (as poor quality images are attempted to be compared). Also, noise in the image can imitate a motion, thereby causing unnecessary and incorrect shift in the image which in turn leads to blur. Further, the amount of motion is inaccurately assessed due to noise—causing incorrect shift in the image—which leads to some residual blur. If, on the other hand, the data is divided into few "time windows," the quality of the data in the frames (or in the image reconstructed from these frames) is good, but the likelihood that at least some of the frames includes data of "before & after" the motion increases.

BRIEF DESCRIPTION OF THE INVENTION

In accordance with various embodiments, a method for imaging is provided. The method includes obtaining image information including timing information and obtaining motion information corresponding to an external movement by a patient being imaged. Obtaining the motion information includes detecting motion of the patient with a sensing device that does not engage the patient. The motion information includes motion timing information. The method further includes associating the motion information with the image information using the image timing information and the motion timing information. The method further includes forming an image representative of a portion of the patient using the associated image and motion information.

In accordance with other embodiments, an imaging system is provided that includes an imaging module, a motion detecting module, and a processing module. The imaging module is configured to perform an image acquisition of a patient to provide imaging data for forming an image of the patient. The imaging data includes image time identification data. The motion detecting module is configured to detect motion in the patient during the image acquisition to provide motion data. The motion data includes motion time identification data. The motion detecting module includes a motion detector that does not engage the patient during a scanning process. The processing module is configured to associate the motion data and the imaging data using at least a portion of the image time identification data and at least a portion of the motion time identification data, and to form an image representative of a portion of the patient using the associate imaging data and motion data.

In accordance with yet other embodiments, a method for medically imaging a patient is provided. The method includes obtaining image information including image timing information and obtaining motion information corresponding to an external movement by the patient. The method also includes associating the motion information with the image information using the image timing information. The method further includes identifying an occurrence of motion, and selecting a type of corrective action to address the occurrence of motion based at least in part upon a time at which the occurrence of motion takes place. The method further includes forming an image representative of a portion of the patient using the associated image and motion information.

DETAILED DESCRIPTION OF THE INVENTION

Figure 1:
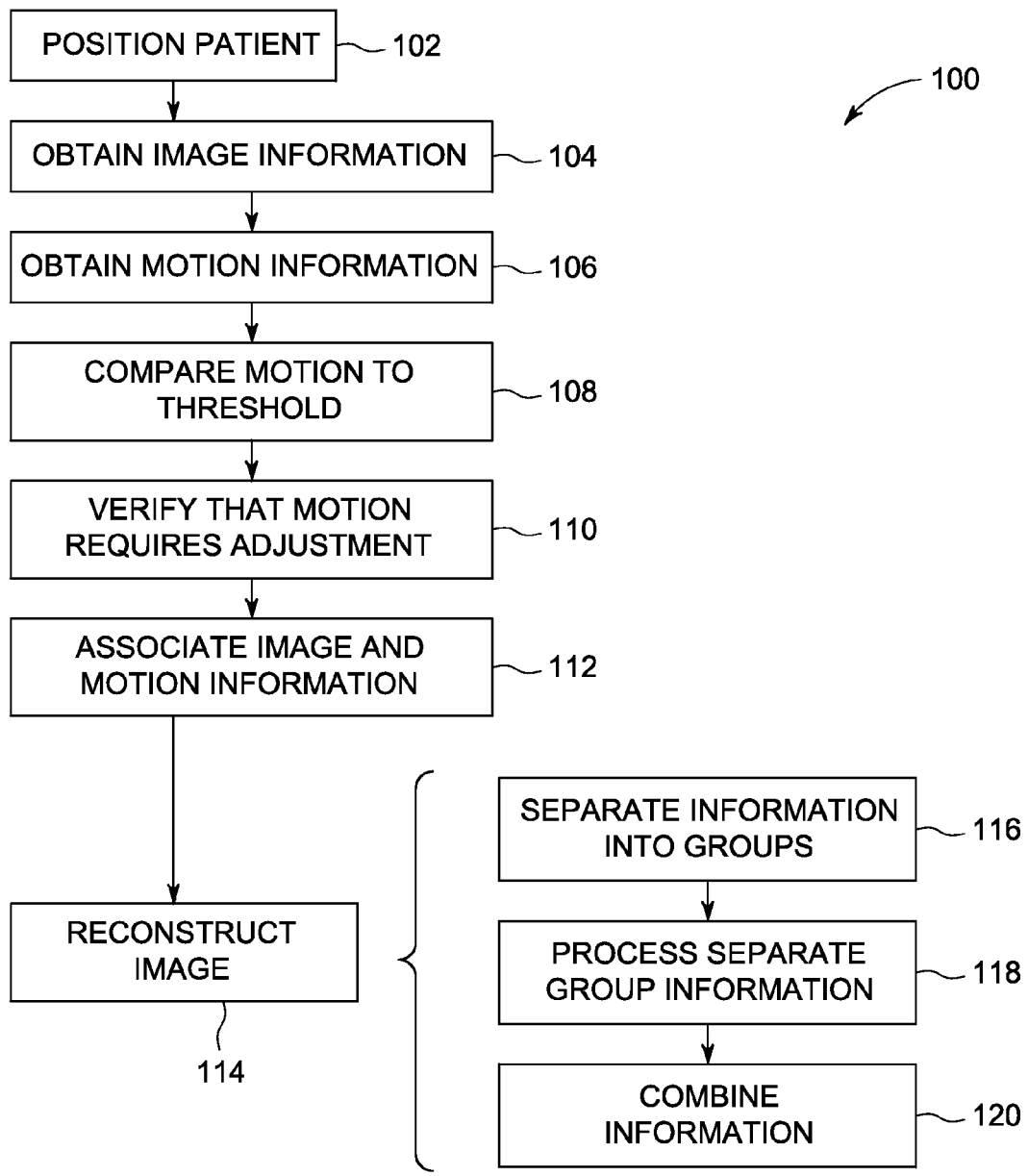
FIG. 1 is a flowchart of a method for medical imaging in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide systems and methods for detection of motion of a patient and association of detected motion with imaging information. In certain embodiments, detected motion information is used to modify the image acquisition process, for example by prolonging image acquisition if motion is detected during a pre-determined stage of image acquisition. In certain embodiments, all or a portion of the imaging information is adjusted during processing to account for motion and to produce an improved image with, for example, less blur. This adjustment is based on motion information associated with the imaging information.

In some embodiments, portions of the imaging information are separated into bins, or groups, based on the motion information associated with a particular portion of the imaging information. The bins may be selected, as examples, based on detected positions or profiles of a patient associated with portions of the imaging information, based on the occurrence and/or the magnitude of movement associated with portions of the imaging information, or based on a stage of a repeated motion, such as caused by breathing. In some embodiments, image information in a particular bin is adjusted (by, for example, a shift in a dataset using registration parameters to account for motion) and then combined with image information to create a combined dataset that can be reconstructed. In some embodiments, each bin is individually reconstructed, the reconstructed images are next registered to each other, and then combined. In certain embodiments, individual frames of imaging information are adjusted.

A technical effect of at least one embodiment is improving image quality and reduction of blur caused by motion or change in position of a subject during imaging. Additionally, patient comfort and convenience can be increased. Further, the need for re-performing an image acquisition due to unsatisfactory formed images may be reduced or eliminated.

In certain embodiments, a motion sensor detects several times when motion occurs. The data is marked accordingly. Only a relatively small number (for example, 1 to 4) of such motions may be found. Then, the data is divided to the fewest "time windows," with each window granted not to include a motion. Then, known techniques may be employed with the "just divided" frames.

FIG. 1 provides a flowchart of a method for medical imaging in accordance with various embodiments. For example, the method 100 may be used to image a portion of interest of a patient using a nuclear medicine (NM) medical imaging technique such as single photon emission computed tomography (SPECT) or positron emission tomography (PET). In other embodiments, different medical imaging techniques, or combinations of techniques, may be used. In various embodiments, certain steps may be omitted or added, certain steps may be combined, certain steps may be performed simultaneously, or concurrently, certain steps may be split into multiple steps, certain steps may be performed in a different order, or certain steps or series of steps may be re-performed in an iterative fashion. For example, various filtering, noise-reduction, or other processing techniques known in the art to form images may also be performed.

After the patient is injected with radiopharmaceutical, at 102, the patient is positioned in a medical imaging system for a scan. For example, a medical imaging system may include a bed or table that supports the patient, and an image detector or detectors (e.g., a gamma camera). The image detectors are configured to obtain or acquire data representative of a subject being scanned, such as a portion of interest of a patient. The image detectors may be stationary or mobile. For example, image detectors may be mounted on a gantry that may be adjusted to a desired position to scan a portion of interest. The gantry may be stationary during the procedure, or may move. Also, in certain embodiments the image detectors may also rotate about the patient. Patient comfort is generally increased by having the bed or table remain generally still, but in certain embodiments the bed or table may also articulate, for example forward/backward and/or up/down, during portions of the scanning process.

With the patient positioned as desired, image information is obtained at 104, for example using a NM technique such as PET or SPECT. The image information corresponds to or is used to depict a portion of the patient being scanned (e.g., isotope concentration in a portion of the body of the patient providing functional information). Further, the image information generally includes image timing information. The timing information identifies the time, or chronological stage, at which particular portions of image information are obtained. For example, the image information may be provided with time stamps or in a list mode. Image acquisition may include a series of data projections that are in turn comprised of a series of discrete instances of image acquisition.

For purposes of the present discussion, information from a discrete instance of image acquisition identified by a time indicator will be referred to herein as a "frame," which may be data acquired from one or more views or projections. It should be noted that a frame may be from a single image detecting device, or may be comprised of information from a plurality of image detecting devices taken at substantially the same time. For example, a frame may include one or more events recorded by one or more gamma cameras with a time stamp. Individual events may be treated as single frames or may be grouped with other similarly time stamped events into a frame. The time indicator, for example, may be an indication of actual or clock time, or, as another example, may be a delta time representative of a time elapsed since the beginning of a scanning process, or referenced from a portion of a scanning process. As another example, each frame may be assigned a frame number or other identifier specifying its place in a sequence of frames, with the timing information including the frame number or other identifier. Optionally, gating information is associated with the frames. For example gating information may include ECG information, such as the time from the last ECG "R-wave," or the relative position in the heartbeat cycle. Similarly, gating information may comprise information about the breathing cycle. Gating information may be used for reconstructing separately images based on frames belonging to the same gating interval within the relevant gating cycle. For example, by selecting and reconstructing a 3D image from all the frames taken at or near the peak diastole, an un-blurred image of the extended heart may be obtained, while selecting and reconstructing a 3D image from all the frames taken at or near the peak systole, an un-blurred image of the contracted heart may be obtained.

At 106 motion information is obtained. In the depicted embodiment, the motion information corresponds to an external motion (e.g., arm or body movement) of the patient being scanned. For example, the motion information may include identifications of specific instances and/or types of movements. As another example, the motion information may include a series of snapshots of positions or profiles of a patient over the course of an image acquisition (e.g., a representation of the physical outline of the patient as recorded by an optical device). With the various positions over the course of an image acquisition known, any changes in position provide information regarding motion. Motion information, as used herein, can thus be understood as information regarding, for example, movement in general, a specific movement or type of movement, information regarding position, or a combination thereof.

The motion information also includes motion timing information. The motion timing information includes a time stamp or other event identifier that may be used to correlate portions of the motion information to portions of the image information, so that any motion or position that is detected may be correlated to a particular frame or frames which were obtained at the same time or substantially the same time as the motion or position. Thus, the particular frame or frames affected by a particular motion or position at a given time or range of time can be associated with that particular motion or position and adjusted accordingly. For example, the motion information may be provided with time stamps or in a list mode that correspond to those used with the image timing information. As another example, the motion information may be provided with a different form of timing information than that used with the image information, as long as the timing information for the motion information and image information can be correlated to each other.

Motion information (e.g., including position information) may be obtained in a variety of ways. For example, the motion may be detected directly or indirectly. In certain embodiments, motion is detected via a remote detecting device that does not contact the patient. For example, motion or position may be detected directly with an optical sensing device, such as, for example, one or more Microsoft® Kinect™ devices, or as another example, a video camera. As another example, motion may be detected directly with a device such as a pressure sensitive mat that contacts, but does not engage, the patient. As one more example, motion may be detected indirectly by detecting a process of the patient being scanned that is typically associated with motion, and estimating an external motion (e.g., discrete positions associated with stages of the process) based upon that process. For example, certain embodiments provide for indirect detection of external motion by measuring a patient's heart rhythm, such as by an electrocardiogram (ECG), and estimating an external breathing motion based on an analysis of the ECG. Breathing cycle may be ascertained from variations in heartbeat rate. Additionally, sudden motion caused by skeletal muscle contraction may be detected as noise or spikes in the ECG signal which is not associated with the normal and predictable cardiac signals. In still other embodiments, various techniques for motion detection may be used in combination. For example, one technique may be used to detect a repeated, anticipated motion such as breathing, with another technique used to detect motions that are not periodic or expected, and/or another technique used to determine if a motion exceeds a threshold value.

Generally speaking, the steps of obtaining motion information and obtaining image information are performed so that the motion information can be associated with the image information for a given instance in time (or, as another example, a given sequence position out of a list or series) that is associated with both the motion and image information. The motion information may be associated with the image information retrospectively, after the entire image acquisition has been performed, or during processing to form an image representative of a portion of the patient. Additionally or alternatively, the motion information may be utilized during the image acquisition process, for example, to prolong the duration of an image acquisition, or to re-perform a particular stage of an image acquisition based upon a detected movement of significant duration, magnitude, or a combination of duration and magnitude.

Figure 2:
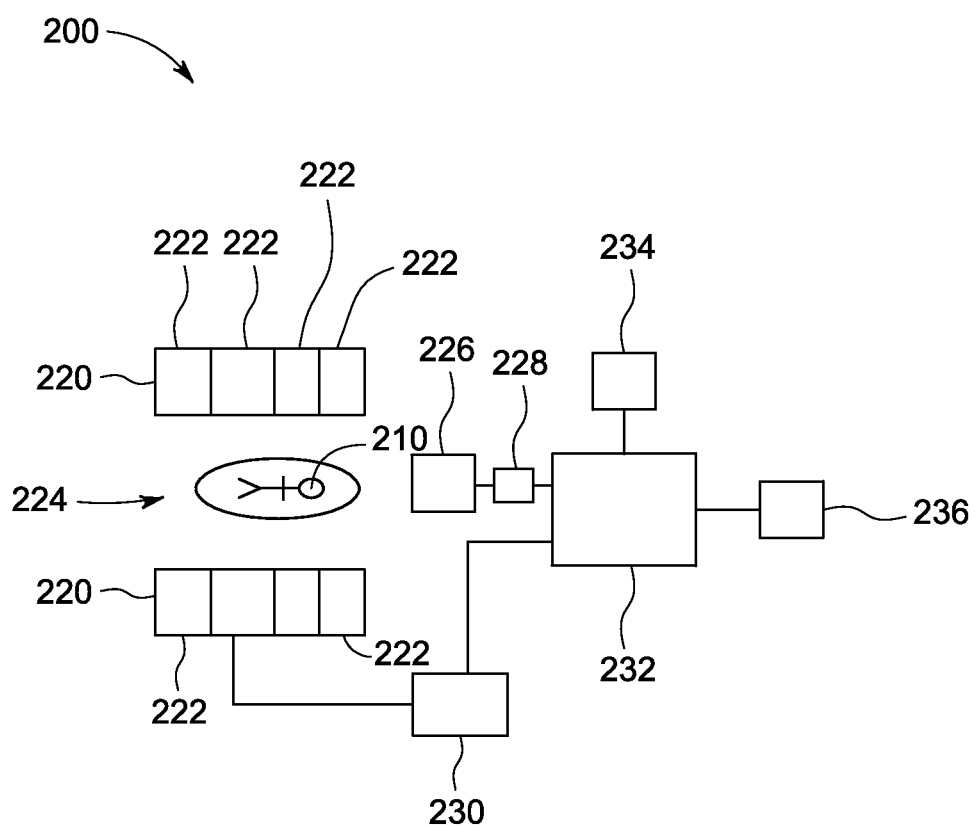
FIG. 2 is a block diagram of an imaging system having a motion detection module in accordance with various embodiments.

The image information may be acquired and processed to reconstruct an image, for example, by an imaging system 200 as shown in FIG. 2. Generally speaking, as discussed in more detail below, the imaging system 200 is configured to obtain image information corresponding to at least a portion of the body of a patient, as well as to obtain motion information corresponding to external motion of the patient during image acquisition. The imaging system 200 is further configured to associate the motion information with the image information. This association may be performed by associating portions of motion and image information that were obtained at the same or nearly the same instance in time. As another example, the association may be performed based on a number identifying a sequence in a list or series that correlates to both image and position information.

The imaging system 200 uses the associated motion information and image information to form an image representative of a portion of the body of interest. For example, in certain embodiments, portions of the image information associated with a particular detected motion are adjusted to account for the particular detected motion before being combined with other portions of the image information to form an image representative of the portion of the body of the patient of interest. In the illustrated embodiment, the imaging system 200 includes detectors 220, a motion detection module 226 and associated motion dataset 228, an image dataset 230, and a processor 232 associated with a memory 234. The imaging system produces image 236 using associated motion and image information obtained via the motion detection module 226 and detectors 220.

The exemplary imaging system 200 includes one or more detectors, such as a pair of detectors 220 having a central opening 224 therethrough. The opening 224 is configured to receive an imaging subject therein, such as a patient 210. In other exemplary embodiments, the detectors 220 include (e.g., are fitted or installed with) pinhole collimators that are arranged about the object to be imaged, such as a patient or a region of interest (e.g., an organ) of a patient. The detectors 220 may be, for example, pixelated detectors configured to operate in an event counting mode. The detectors 220, for example pixelated detectors, may be configured to acquire SPECT image data. In some embodiments, including the illustrated embodiment, a plurality of detector modules 222 are provided, each having a plurality of pixels and forming a detector 220. In various embodiments, one or more detectors may be used. Further, one or more detectors may articulate with respect to the patient. For example a detector may rotate about a patient and/or be articulated linearly with respect to the patient during image acquisition. The detectors 220 collect information representative of a patient and output an image dataset 230. In the illustrated embodiment, the detectors 220 acquire a series of images over time as frames that are each associated with a corresponding time stamp identifying a point in time at which a particular frame was obtained, and output image dataset 230 including frame-by-frame image information and corresponding timing information.

The motion detection module 226 includes one or more motion detection devices. Generally speaking, the motion detection module 226 is configured to obtain information at least one of recognizing, identifying, describing, depicting, or characterizing an external movement and/or position of the patient during the image acquisition, and to output a motion dataset 228. In the depicted embodiment, the motion dataset 228 includes motion information corresponding to external motion by a patient, and motion timing information associating portions of the motion information with corresponding time stamps identifying points in time at which particular portions of the motion information were obtained. In certain embodiments, the motion detector may detect movement and/or position generally continuously with an associated time stamp. In other embodiments, only actual movement or changes in position may be detected and associated with a time stamp, while periods of time without motion or without deviation from a reference position, for example an initially determined base position, are not included in the motion dataset 228. In certain embodiments, discrete instances of motion detection substantially coincide with the timing of the frames during which image information is acquired.

Figure 3:
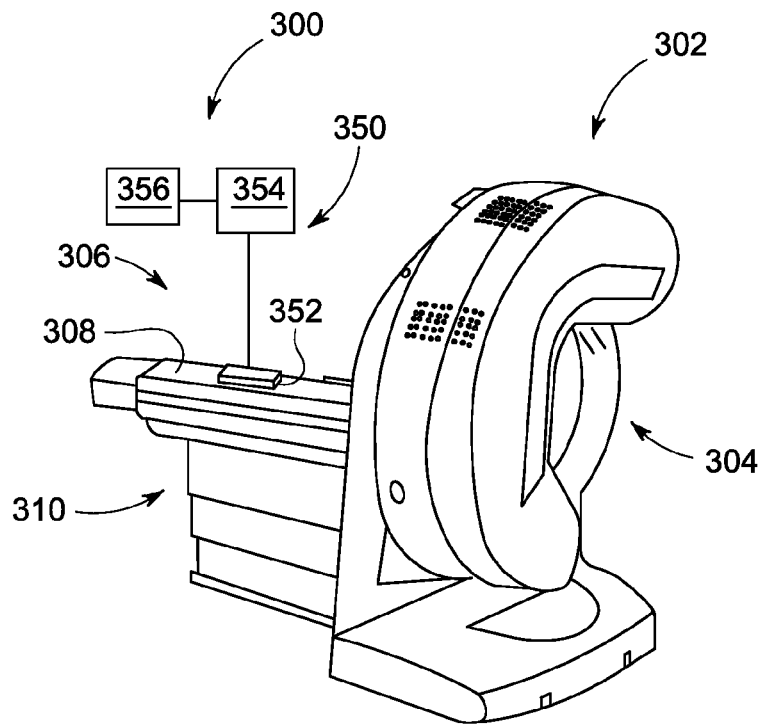
FIG. 3 is a diagram of an imaging system having a motion detection module in accordance with various embodiments.

FIG. 3 illustrates a system 300 for detecting motion of a patient being imaged. For example, the illustrated system 300 may be a NM imaging system, which is shown embodied as a SPECT imaging system. The system 300 includes an integrated gantry 302 having a gantry central bore 304. The gantry 302 is configured to support one or more NM radiation detectors (e.g., a multi-pinhole camera configuration), which may be configured as a pair of detectors (such as detectors 220 discussed above) that are supported, for example, around 180 degrees of the gantry 302. In such a configuration, the system may include multiple imaging detectors with collimators that are arranged about the object to be imaged, instead of two detectors spaced apart 180 degrees. It should be noted that the NM radiation detectors may be supported around more or less of the gantry 302, for example, around the entire 360 degrees of the gantry 302. Thus, the radiation detectors are arranged around the gantry central bore 304 defining an examination axis.

A patient table 306 may include a bed 308 slidingly coupled to a bed support system 310, which may be coupled directly to a floor or may be coupled to the gantry 302 through a base coupled to the gantry 302. The bed 308 may include a stretcher slidingly coupled to an upper surface of the bed 308. The patient table 306 is configured to facilitate ingress and egress of a patient (not shown) into an examination position that is substantially aligned with the examination axis of the gantry central bore 304. During an imaging scan, the patient table 306 may be controlled to move the bed 308 and/or stretcher axially into and out of (as well as upward and downward within) the gantry central bore 304, such as prior to obtaining image information for the patient or a region of the patient, when the table is then stationary. It should be noted that the various embodiments may be implemented in connection with imaging systems that include stationary gantries or moving gantries, or other types of imaging systems.

The system 300 also includes a motion detection module 350 comprising a mat 352 and a motion detection processor 354. The motion detector processor 354 may be a dedicated unit, or may be incorporated into a processor or similar device associated with all or a portion of other parts of an imaging system. The mat 352 is positioned on the bed 308 so that all or a portion of a patient rests atop the mat 352 during the image acquisition. In alternate embodiments, a mat or other sensing device may be placed underneath a resting surface for a patient, so long as the mat is able to detect a desired amount of motion with the interposed material in place. The mat 352 is an example of a device that detects motion and contacts a patient, but does not engage a patient. Examples of devices that engage a patient include, for example, devices that are worn by a patient, wrapped around a patient (such as a strap), or otherwise be affixed to a patient.

By not engaging or otherwise confining the patient, the mat 352 increases patient comfort and convenience compared to systems that engage a patient, such as systems that use a strap that surrounds a patient. The mat 352 is operably connected to the motion detection processor 354, and information from the mat 352 is sent to the motion detection processor 354, which provides a time stamp based upon a time at which that information is received or obtained, and creates a motion dataset 356 that includes information corresponding to motion as well as times at which motions occurred. The motion dataset 356 is output, for example, to a processor such as processor 232, discussed below.

In an exemplary embodiment, the mat 352 comprises a fluid-filled pad along with a transducer for detecting, for example, a pressure change of the fluid, or as another example, motion and/or sound transmitted through the fluid. Such a detector as mat 352 provides information regarding external movements of a patient, but may not provide as detailed or descriptive information as other systems, such as the system 400 discussed below.

Figure 4:
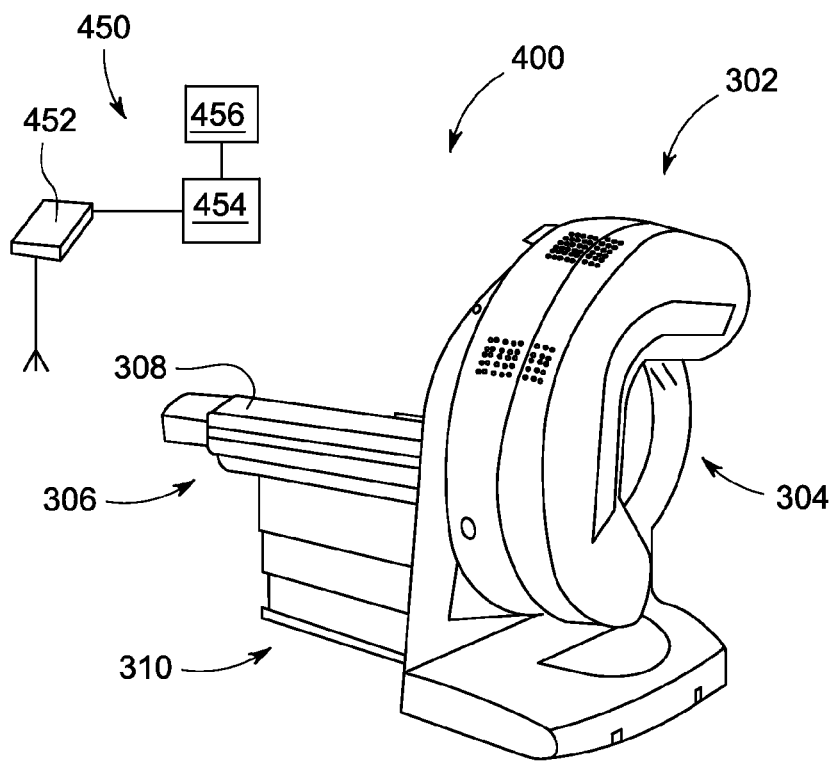
FIG. 4 is a diagram of an imaging system having a motion detection module in accordance with other various embodiments.

For example, in other embodiments, motion detection is performed by a motion detecting system that optically detects motion. FIG. 4 illustrates a system 400 including such a device. The embodiment of FIG. 4 resembles the system 300 previously discussed in certain respects. Certain common aspects will not be repeated here, but will be understood by one skilled in the art based on the above discussion, with like numbers in FIG. 4 corresponding to the above description regarding the system 300. The motion detection system 400 includes a motion detection module 450 including an optical detection device 452 and a motion detection processor 454. The motion detection module 450, for example, may include one or more Microsoft® Kinect™ devices. The optical detection device 452 does not sense via direct or indirect physical contact, and provides an example of a remote detection device. Information from the optical detection device 452 is provided to the motion detection processor 454, which associates timing information with the information provided from the optical detection device to create a motion dataset 456. The motion detection processor 454 may perform additional processing, and outputs the motion dataset 456 to a processor, such as processor 232, for further processing, for example as discussed elsewhere herein.

Motion information (including, for example, positions of the patient acquired over a time range) from the optical detection device 452 may be provided in a variety of ways. For example, a profile of a patient or portion of interest of a patient may be obtained at each discrete time interval at which frames are obtained during image acquisition by the detectors 220. After image acquisition, for example at a processor such as the processor 232, each frame may subsequently be associated with the profile obtained by the optical detection device 452 at the corresponding time. Then, for example, the profiles may be analyzed and the information divided into groups, with frames included in sets or subsets according to profile type for further processing. For example, a group of frames corresponding to a first position of a patient (for example, with a ribcage in a high position during a portion of a breathing cycle) can be placed in a first group, while a group of frames corresponding to a second position of a patient (for example, with a ribcage in a low position during a different portion of the breathing cycle) can be placed in a second group. Of course, more or different groups based on various positions of a patient may be used. In certain embodiments, each group or subset based upon a given profile may be individually reconstructed, with the reconstructed images registered to each other and then combined. In other embodiments, for example, registration parameters may be used to shift subsets to construct a consistent combined (or re-combined) dataset that can be reconstructed with reduced blur.

In alternate embodiments, a base profile, for example, the starting position of a patient, is determined. For any frames that are taken with the patient determined to be substantially in the base position, the motion information may be disregarded. However, for those frames that are taken with motion determined sufficient enough to require further processing, such frames are associated with the motion information for the corresponding time for further processing. For example, such frames, or groups of frames as discussed above, may be characterized by profile (such as an outline of the patient as determined by the optical detection device), and adjusted accordingly to account for the detected motion (for example, by adjusting based on a comparison of anatomical landmarks in the frames with motion and the frames without motion), and then re-combined with the information taken with the patient in the base, or original, position. Profiles varying from the base position may occur repeatedly and/or periodically, such as a change in the outline or shape of a patient based on breathing motions, or may occur only once and/or non-periodically, such as a shift in weight or other movement or adjustment by an uncomfortable patient having difficulty remaining still for the required time. In certain embodiments, if the number of frames affected by motion is sufficiently small, and if the number of frames not affected by motion provide enough information to form a satisfactory image, some or all of the frames affected by motion may be disregarded.

In still other embodiments, an external motion of a patient is detected indirectly. For example, one common type of patient motion during image acquisition is caused by breathing. Typically, during inspiration (inhaling of air into the lungs), the diaphragm descends and the ribcage elevates and/or expands. Similarly, during expiration (exhaling of air out of the lungs), the diaphragm ascends and the ribcage descends and/or contracts. Thus, the breathing cycle may be broken down into different phases, or stages, that will generally contain similar body positions. For example, in certain embodiments, four stages of the breathing cycle are used, namely, the beginning portion of inspiration, the end portion of inspiration, the beginning portion of expiration, and the end portion of expiration. These stages may be generally continuous (for example, the beginning portion of inspiration may considered the first half of inspiration and the end portion of inspiration may be considered the second half of inspiration); or there may be gaps so that not all portions of the breathing cycle are included in one of the stages, or groups. In other embodiments, different numbers of stages may be used.

During subsequent processing as part of reconstructing an image, all of the image information associated with motion information corresponding to a particular stage of the breathing cycle may binned, or placed into a group or subset, based on that particular stage. Thus, for example, in embodiments utilizing four stages of a breathing cycle, four corresponding bins would be used to process the image information, with image information being placed into a particular bin based upon the portion of the breathing cycle during which that image information was obtained (determined based upon associated motion information corresponding to the time at which the image was obtained). The bins may then be processed to be synchronized to reduce blur. In certain embodiments where one bin or a group of bins less than all of the bins provides enough information to satisfactorily form an image, some of the bins may be disregarded.

Figure 5:
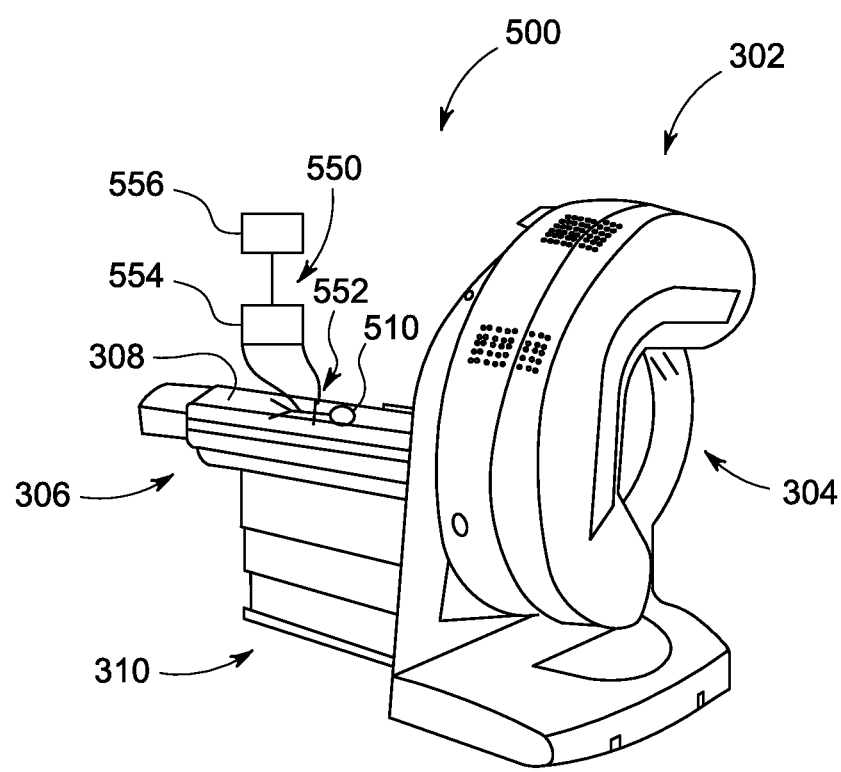
FIG. 5 is a diagram of an imaging system having a motion detection module in accordance with other various embodiments.

FIG. 5 illustrates an embodiment that employs such an indirect detection. FIG. 5 illustrates a system 500 utilizing cardiac measurement to indirectly detect breathing motion of a patient 510. The embodiment of FIG. 5 resembles the system 300 previously discussed in certain respects. Certain common aspects will not be repeated here, but will be understood by one skilled in the art based on the above discussion, with like numbers in FIG. 5 corresponding to the above description regarding the system 300. The motion detection system 500 includes a motion detection module 550 including electrocardiogram (ECG) sensors 552 and a motion detection processor 554.

The sensors 552 are operably connected to the motion detection processor 554, and information from the ECG sensors 552 is provided to the motion detection processor 554, which associates timing information with the information provided from the sensors to create a motion dataset 556. The motion detection processor 554 may perform additional processing, and outputs the motion dataset 556 to a processor such as processor 232 for further processing. For example, a stage or phase of the breathing cycle may be determined by variations in the r-r interval and/or the q-r interval. This information regarding the cardiac cycle may be received from the sensors 552 and used to identify a corresponding portion of the breathing cycle by the motion detector processor 554, which may then associate at least a portion of the time stamps with a corresponding phase or stage of the breathing cycle. Thus, at least a portion of the frames of image information (obtained, for example, by detectors 220) can be subsequently associated with the motion information (and therefore associated with corresponding stages of the breathing cycle), and placed into bins for processing as discussed above.

Returning to FIG. 2, the processor 232 inputs the image dataset 230 and motion dataset 228, associates the image dataset 230 and motion dataset 228, and forms an image using the associated data. Using, for example, time stamp information from each dataset, the processor 232 associates portions of the image dataset 230 with corresponding portions of the motion dataset 228, with portions having corresponding time stamps (or other corresponding timing information) being associated together. Thus, the processor 232 is able to determine which frames of the image information were taken at different motion or position conditions (e.g. no motion, a position as identified by a profile recognized by an optical detector, a portion of the breathing cycle, etc.) and process the frames accordingly.

The processor 232 may then adjust frames individually based on motion information associated with the individual frames (such as, for example, a motion identified by a movement of an anatomical landmark compared with one or more other frames) by shifting a dataset associated with that frame an appropriate amount for combination with the one or more other frames. In other embodiments, the processor 232 may group frames having similar associated motion information together to account for motion effects and reduce blur. For examples, groups may be determined based upon stage of the breathing cycle, with frames assigned to bins based upon stage of breathing cycle. As another example, frames may be grouped based upon the shape of profile or physical outline of the patient as detected by an optical detecting device, with frames assigned to bins, with each bin corresponding to a general shape or profile so that generally similar frames are binned together. In certain embodiments, each bin is individually reconstructed, with the reconstructed images registered to each other (using, for example, known registration techniques or algorithms) and then combined, for example, for noise reduction. The reconstructed images may be re-combined, for example, by addition or weighted averaging. In other embodiments, frames in a given bin are adjusted individually or as a group, and then added to the other frames to form a combined dataset, which is then reconstructed. In such embodiments, for example, registration parameters may be used to shift data subsets.

It should be noted that the data, either raw or processed, such as the image dataset or motion dataset or portions thereof, may be stored for a short term (e.g., during processing) or for a long term (e.g., for later offline retrieval) in a memory 234. The memory 234 may be any type of data storage device, which may also store databases of information. The memory 234 may be separate from or form part of the processor 232. In certain embodiments, processors associated with, for example, image detectors and/or motion detectors may also have separate or shared memories.

Returning to method 100, at 108 the magnitude of motion is compared to a threshold, with the motion information only associated with the image information if the threshold is met or exceeded. Thus, relatively minor motions that will not materially affect image quality can be disregarded or ignored in the depicted embodiment. This comparison may be performed, for example, by a motion detection processor, such as 354, 454, or 554, which may disregard motions beneath the threshold and only include motions meeting or exceeding the threshold in the motion dataset output to a processor for subsequent association and reconstruction of an image. In other embodiments, for example, the comparison may be made by a processor (such as the processor 232) receiving the image and motion datasets, with the processor only associating image information and motion information for those portions of the motion information with a motion satisfying the threshold criteria. The magnitude of the motion may be determined, for example, by a degree of change in the profile as detected by the optical motion detector 452 compared to a base profile, or as another example, by the amount of pressure change experienced by a device such as mat 352. Thus, in certain embodiments, a group of frames for which no adjustment is to be made may be separated from a group or groups of frames which will be adjusted to account for motion effects.

At 110, image information identified as having motions satisfying the threshold are analyzed to verify that the images require adjustment. This step may be performed, for example, by a processor such as processor 232. Those frames for which it is determined no adjustment will be made may be re-grouped with a base group, for example. The frames for which the analysis determined that additional adjustment will be made may be retained for further processing, either individually or by group. In certain embodiments, as discussed more fully below, detection of a motion exceeding a threshold may result in the modification of the image acquisition process, for example, by prolonging a duration of the image acquisition process or performing additional scans.

At 112, the motion information and image information are associated, as also discussed elsewhere herein. Generally speaking, the motion information includes motion timing information, and the image information includes image timing information. Portions of the motion information and image information having corresponding timing information are associated together, thereby linking frames with corresponding motion information. For example, each frame may be associated with a profile of the patient obtained at the same or similar time at which the frame was obtained. As another example, each frame may be associated with a substantially co-incident portion of a breathing cycle as detected, directly (for example, based on profiles obtained by an optical detection unit), or indirectly (for example, based upon ECG data). In certain embodiments, all frames of the image information may be associated with motion information, while in other embodiments only a portion of image information may be associated with motion information. For example, only image information associated with motion exceeding a threshold may be associated with motion information.

At 114, the associated motion and image information are used to form or reconstruct an image. Adjustment or modification of data, for example, in certain embodiments is performed based on a comparison of anatomical landmarks between a frame to be adjusted and a base frame, or frame that does not need to be adjusted. The shift, or amount of adjustment and/or type of adjustment, is determined based on the amount and/or type of difference between the position of the anatomical landmark for the frame to be adjusted and the base frame. With the identified motions accounted for in the adjusted frames, the adjusted frames may be combined with the frames that were not adjusted into a combined dataset, which may then be reconstructed as part of reconstructing an image. In other embodiments, all or a portion of the frames are grouped into bins, with each bin containing generally similar frames based on the motion information associated with the particular frames. Thus, information may be adjusted on an individual frame basis, on a group-by-group basis, or a combination thereof. For example, in the embodiment depicted in FIG. 1, step 114 comprises steps 116, 118, and 120.

At 116, image information is separated into groups for further processing. For example, different types of motions or positions may be identified in the motion information associated with the image information, with the image information for each type of position or motion placed into a bin dedicated to that type of position nor motion. As one example, in certain embodiments, four bins are established, each for a separate stage of a breathing cycle. Portions of the image information acquired during a particular stage of the breathing cycle (as identified, for example, by the associated motion information) are grouped together in a bin dedicated to image information for that particular stage of the breathing cycle. As another example, bins may be dedicated for given positions or profiles of a patient acquired by an optical motion detection module. For example, during image acquisition, a motion detection module may categorize all identified positions into groups of similar positions, with a first type of generally similar positions being place in one bin, a second type of generally similar positions placed in another bin, and so on. The groups may be pre-determined (for example, a given range of levels of ribcage elevation associated with a stage of a breathing cycle) or may be determined based upon an analysis of the recorded profiles of a given scan to accommodate, for example, any unexpected or not easily predictable movements by a patient.

Binning, or grouping, thus may be organized in a variety of ways. As examples, groups may be organized according to magnitude of detected motion or change of position, according to pre-determined positions, according to positions identified by an analysis of the obtained motion information, according to stages of a breathing cycle as detected directly by an optical detection unit or as detected indirectly by analysis of an ECG, according to movement identified by a sensor pad or mat, by presence or absence of motion, or a combination thereof.

Next, at 118, data for at least some of the bins, or groups, is adjusted to process separate group information for each group. For example, in certain embodiments, in a group of frames characterized by a particular shift from a base position, each frame in the group may be adjusted by that particular shift, with the separate groups, once adjusted, combined together for subsequent reconstruction (for example, at 120 below). In other embodiments, each group or bin, or at least a number of the groups or bins, may be individually reconstructed to form a plurality of reconstructed bin images. Then, the reconstructed bin images are registered to each other, for example using known registration techniques, and then subsequently combined. Thus, the groups may be adjusted separately and then reconstructed in certain embodiments, and adjusted and reconstructed separately and then combined in certain other embodiments. Further, in certain embodiments, some bins or groups may not be adjusted while other bins or groups are. For example, in certain embodiments a base group corresponding to a predetermined or frequently occurring position or movement may not be adjusted. As another example, in some embodiments, a bin that contains a sufficiently small amount of information may be disregarded. For example, in embodiments, bins that contain relatively small amounts of motion or change of position may be adjusted, while bins that contain relatively large amounts of motion or change of position may be disregarded. Further, different techniques may be used to adjust different bins within a given embodiment. Thus, in various embodiments, some bins may be adjusted while others are not, bins may be adjusted by similar or different techniques, and still other bins may be disregarded.

At 120, the separate group information is combined to form an image representative of a portion of the body of interest. As also indicated above in connection with step 118, in certain embodiments combining the group information includes combining the separate group information into a combined dataset that is then reconstructed. In certain other embodiments, combing the group information includes combining reconstructed images that have been generated from each separate bin.

Figure 6:
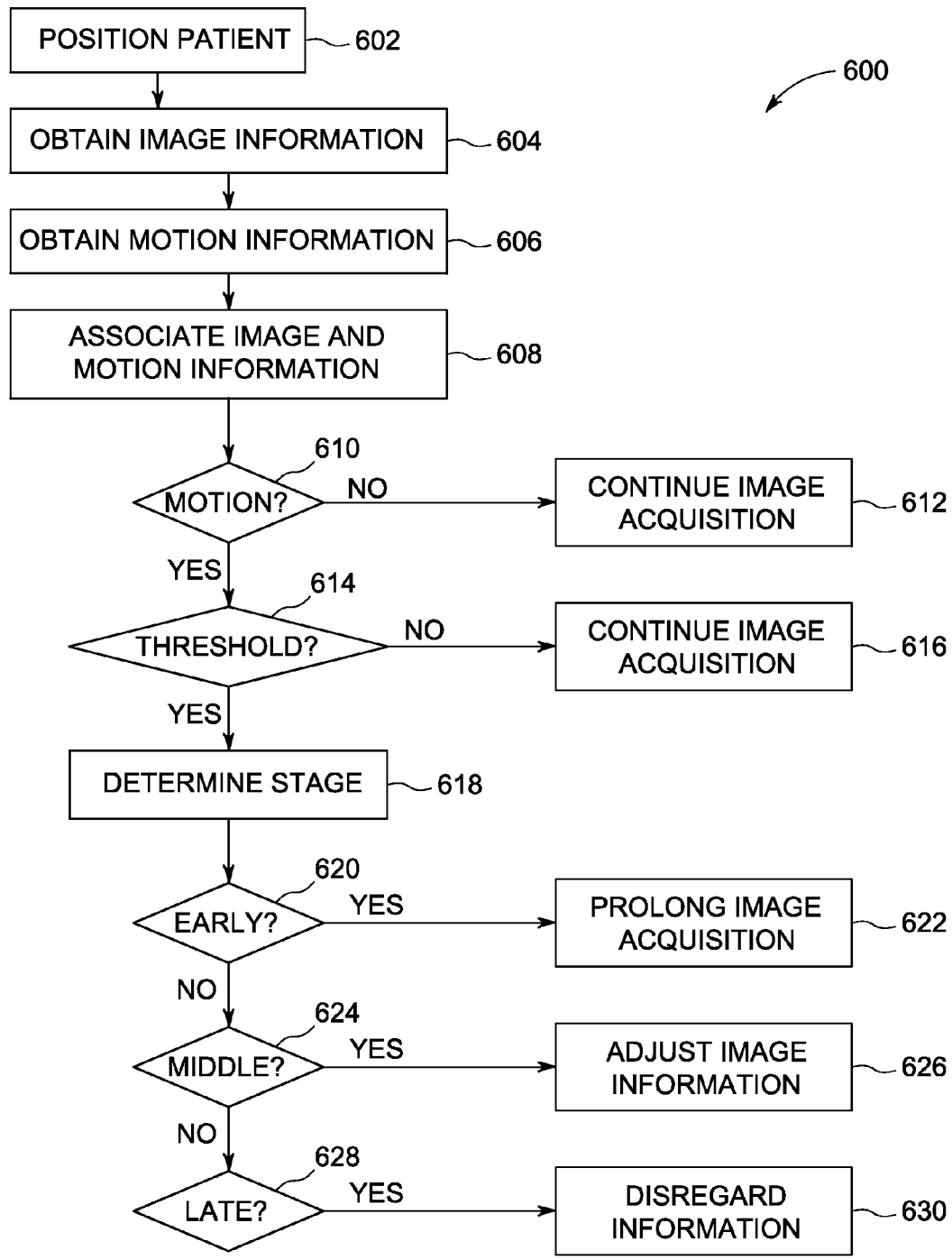
FIG. 6 is a flowchart of a method for medical imaging in accordance with various embodiments.

As indicated above, certain embodiments provide for allowing adjustments to the image acquisition process (alternatively or additionally to adjustments to image reconstruction subsequent to image acquisition) to account for motion of a subject during image acquisition. FIG. 6 illustrates a flowchart of an embodiment of a method for imaging that provides for adjustments to the image acquisition process to account for motion. The method 600 uses motion detection information to adjust the performance of image acquisition. In various embodiments, certain steps may be omitted or added, certain steps may be combined, certain steps may be performed simultaneously, or concurrently, certain steps may be split into multiple steps, certain steps may be performed in a different order, or certain steps or series of steps may be re-performed in an iterative fashion. For example, in certain embodiments, aspects of the method 600 can be joined in various combinations with steps from the method 100 discussed above. Also, for example, image acquisition to obtain additional image information may continue while previously obtained information is analyzed according to one or may steps of the method 600.

At 602, a patient is placed in a desired position. This may be accomplished generally similarly to step 102 discussed above. Then, at 604, image information may be obtained, for example as discussed above. Similarly, at step 606 motion information may be obtained, for example as also discussed above.

At 608, the image information is associated with the motion information. In certain embodiments, all frames of the image information may be associated with motion information, while in other embodiments only a portion of image information may be associated. In certain embodiments, this step may occur at a different, later stage of a process.

At 610, the presence of absence of motion is determined. This may be detected, for example, by detecting a change in pressure by a pad or mat, or as another example, a change in position as detected by an optical detector. If no motion is detected, the image acquisition may continue without adjustment (step 612).

If motion was detected, it is next determined if the motion exceeds a threshold at step 614 threshold. The threshold is set so that motion that will not sufficiently affect image reconstruction may be disregarded, while motion that will sufficiently affect image reconstruction may be addressed. In certain embodiments, steps 610 and 614 may be performed simultaneously, or concurrently. For example, a detector may be configured so that any motion detected is considered sufficient and is above a determined threshold. If the detected motion is not sufficient to satisfy a threshold, the image acquisition may continue without adjustment (step 616).

If the motion detected satisfies the threshold, at 618 the stage of the image acquisition at which the motion is detected is determined. In the depicted embodiment, the image acquisition is characterized by three stages determined by time of image acquisition: a first, early stage of image acquisition; a second, middle stage of image acquisition; and a third, ending stage of image acquisition. Other numbers or types of stages may be employed in different embodiments. Further still, each stage may have a different threshold associated with it. For example, one threshold may be used in connection with prolonging image acquisition, a second threshold used in connection with data adjustment, and a third threshold used in connection with disregarding information.

At 620, if the motion is detected in an early stage of the image acquisition, the image acquisition is prolonged at step 622. In certain embodiments, it may still be relatively convenient to prolong a scan if a problem is detected at the beginning of the scanning compared to if it is detected later in the scan. The benefit of acquiring images without need for adjustment (or reduced need for adjustment) may justify prolonging the image acquisition. In certain embodiments, the determination regarding whether to prolong the image acquisition process is based at least upon a quantity and/or a magnitude of detected motion during an early stage of image acquisition.

At 624, if the motion is detected in a middle stage of the image acquisition, the image information affected by the motion is adjusted at 626. In the depicted embodiment, the middle stage is selected as a time period where it is more beneficial to adjust data than to attempt to prolong or re-start the image acquisition process. This adjustment of data may be performed, for example, as discussed elsewhere herein. This adjustment may take place while image acquisition continues (for example, certain portions of the image information are adjusted while other portions are being obtained), or may be adjusted after image acquisition (for example, as part of a binning or grouping process as discussed above).

At 628, if the motion is detected in a late stage of the image acquisition, the image information affected by the motion is disregarded at 630. For example, enough information may have already been obtained to sufficiently form a satisfactory image. In certain embodiments, the determination regarding whether to disregard image information affected motion during an ending, or late, stage of image acquisition is based at least upon a quantity and/or quality of image information that has already been obtained during the image acquisition.

Once image acquisition is complete, the obtained and associated information is used to form an image, for example as discussed elsewhere herein. The stages and corresponding corrective responses discussed above are illustrative and not exhaustive. For example, different corrective responses may be used for the individual stages discussed above, different stages may be used, more than one stage may employ the same corrective response or a generally similar corrective response or type of response, and more than one corrective response may be associated with any given stage. In certain embodiments, for example, in forming the image, only portions of information obtained during a given stage, such as the middle stage, may be adjusted, while information obtained in other stages is not adjusted. In certain embodiments, portions of information from a plurality of stages may be adjusted. For example, a higher threshold (or thresholds) may be used to determine if image acquisition is prolonged in an early stage and if information is disregarded in a later stage, while a different, lower threshold is used to determine if information is adjusted. Thus, a given portion of the motion information may correspond to a motion that was not substantial enough to warrant prolonging image acquisition or disregarding of information, but was substantial enough to warrant adjustment.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for imaging, the method comprising:
    obtaining image information including image timing information;
    obtaining motion information corresponding to an external movement by a patient being imaged, the motion information including motion timing information, wherein obtaining the motion information comprises detecting motion of the patient with a sensing device that does not engage the patient;
    generating an associated image by associating the motion information with the image information using the image timing information and the motion timing information; and
    forming an image representative of a portion of the patient using the associated image and motion information;
    wherein obtaining motion information comprises estimating a breathing motion based upon a sensed heart rhythm, the method further comprising: dividing the image information into a plurality of groups, each group representing a portion of a breathing cycle; processing the plurality of groups separately to form separate group image information; and forming a combined image using the separate group image information.

2. A method in accordance with claim 1, wherein obtaining the motion information comprises detecting motion of the patient with a pad placed beneath the patient.

3. A method in accordance with claim 1 wherein obtaining the motion information comprises detecting motion of the patient without contacting the patient.

4. A method in accordance with claim 1 wherein a portion of the image information is disregarded based at least upon the motion information.

5. A method in accordance with claim 1 wherein an additional time period of obtaining image information is performed based at least upon the motion information.

6. A method in accordance with claim 1 wherein forming an image using the associated image and motion information comprises adjusting at least a portion of the image information using the motion information.

7. A method in accordance with claim 1 further comprising determining a magnitude of movement based on a portion of the motion information, and comparing the magnitude of movement with a pre-determined threshold to determine if the portion of the motion information will be associated with the image information.

8. A method in accordance with claim 1 wherein forming an image using the associated image and motion information comprises grouping at least portions of the image information into groups based upon the motion information, processing separate group information for each of the groups, and forming a combined image using the separate group information.

9. A method for medically imaging a patient, the method comprising:
    obtaining image information including image timing information;
    obtaining motion information corresponding to an external movement by the patient;
    generating an associated image by associating the motion information with the image information using the image timing information;
    identifying an occurrence of motion;
    selecting a type of corrective action to address the occurrence of motion based at least in part upon a time at which the occurrence of motion takes place; and
    reconstructing an image representative of a portion of the patient using the associated image and motion information;
    wherein obtaining motion information comprises estimating a breathing motion based upon a sensed heart rhythm, the method further comprising:
    dividing the image information into a plurality of groups, each group representing a portion of a breathing cycle;
    processing the plurality of groups separately to form separate group image information; and
    forming a combined image using the separate group image information.

10. A method in accordance with claim 9 wherein image acquisition is prolonged based at least in part upon if the identified occurrence of motion takes place during a pre-determined phase of obtaining image information.

11. A method in accordance with claim 9 wherein image information associated with the occurrence of motion is adjusted based at least in part upon if the occurrence of motion takes place during a pre-determined phase of obtaining image information.

12. A method in accordance with claim 11 wherein image information associated with the identified occurrence of motion is processed separately from image information not associated with any occurrence of motion to provide adjusted image information, and the adjusted image information is subsequently combined with the image information not associated with any occurrence of motion.

13. A method in accordance with claim 9 wherein image information associated with the occurrence of motion is disregarded based at least in part upon if the occurrence of motion takes place during a pre-determined phase of obtaining image information.

* * * * *